(12) United States Patent
Dalle Carbonare

(10) Patent No.: US 8,487,007 B2
(45) Date of Patent: Jul. 16, 2013

(54) PHARMACEUTICAL FORMULATION CONTAINING PALMITOYL ETHANOLAMIDE AND STEAROYL ETHANOLAMIDE

(75) Inventor: Maurizio Dalle Carbonare, Vicenza (IT)

(73) Assignee: Vermont Italia SRL, Vicenza (IT)

( * ) Notice: Subject to any disclaimer, the term of this patent is extended or adjusted under 35 U.S.C. 154(b) by 135 days.

(21) Appl. No.: 12/989,786

(22) PCT Filed: Apr. 28, 2008

(86) PCT No.: PCT/IT2008/000292
§ 371 (c)(1),
(2), (4) Date: Oct. 28, 2010

(87) PCT Pub. No.: WO2009/133574
PCT Pub. Date: Nov. 5, 2009

(65) Prior Publication Data
US 2011/0046225 A1    Feb. 24, 2011

(51) Int. Cl.
*A61K 31/16* (2006.01)
*A61P 17/00* (2006.01)
*A61P 17/04* (2006.01)
*A61P 17/10* (2006.01)
*A61P 15/02* (2006.01)
*A61P 15/00* (2006.01)
*A61P 29/00* (2006.01)
*A61P 17/08* (2006.01)
*C07C 233/18* (2006.01)
*A61K 31/164* (2006.01)

(52) U.S. Cl.
USPC .......................................... 514/625; 554/66

(58) Field of Classification Search
USPC ....................................................... 514/625
See application file for complete search history.

(56) References Cited

U.S. PATENT DOCUMENTS

| | | | |
|---|---|---|---|
| 2,394,833 A | | 2/1946 | Young et al. |
| 5,506,224 A | * | 4/1996 | della Valle et al. ........... 514/182 |
| 6,083,536 A | | 7/2000 | Macrides |

FOREIGN PATENT DOCUMENTS

| | | |
|---|---|---|
| WO | 9960987 | 12/1999 |
| WO | 2008023998 | 2/2008 |
| WO | 2008075978 | 6/2008 |

OTHER PUBLICATIONS

Dalle Carbonare M. et al., A saturated N-acylethanolamine other than N-palmitoyl ethanolamine with anti-inflammatory properties: A neglected story . . . , Journal of Neuroendocrinolgy, vol. 20, No. Suppl. 1. May 2008, pp. 26-34, Abstract.
PCT, International Search Report, Apr. 23, 2009.
Nunzio Sepe et al., Bioactive long chain N-acethanolamines in five species of edible bivalve molluscs, Biochimica et Biophysica Acta 1389 (1998).
F. Benvenuti et al., Attivita' di alcuni derivati della palmitoletanoamina sull'edema nella zampa di ratto, Istituto Sieroterapico e Vaccinogeno, 1967, 809-813.

\* cited by examiner

*Primary Examiner* — Sreeni Padmanabhan
*Assistant Examiner* — Jason A Deck
(74) *Attorney, Agent, or Firm* — Themis Law

(57) ABSTRACT

The invention concerns new pharmaceutical formulations containing a blend of palmitoyl ethanolamide or PEA and stearoyl ethanolamide or SEA compounds as active principles. The formulation is suitable for oral, parenteral, topical, transdermic, rectal, sublingual, nasal, topical, transdermic, rectal, nasal or sublingual administration, whereby the dosage form of said formulations can be in patches, suppositories, ovules, pessaries, aerosol or spray, emulsions, suspensions, solutions. Said pharmaceutical formulations are useful for the treatment or prevention of skin pathologies, for the treatment or prevention of gynaecological pathologies, for the treatment of disorders or pathologies characterized by improper metabolism of fatty acids as well as for the treatment of disorders or pathologies characterized by inflammatory states

9 Claims, No Drawings

PHARMACEUTICAL FORMULATION CONTAINING PALMITOYL ETHANOLAMIDE AND STEAROYL ETHANOLAMIDE

Cannabinoids, which contain the primary active principle of cannabis i.e. delta-9-tetrahydrocannabinol (THC), have been long-known to have, further to their psychoactive effects, pharmaceutical properties of interest in the treatment of a number of different pathologies or the symptomatologies they are associated with (Ameri A., 1999 Progress in Neurobiol. 58: 315-348).

Amongst the foregoing, concrete experimental evidence nowadays shows that cannabinoids such as e.g. cannabidiol or other derivatives of THC are capable of exerting pain killing and anti inflammatory effects in acute or chronic pathologies, also of the autoimmune type, occurring in different body sections, associated with inflammation and/or algic conditions such as e.g. arthritis, including rheumatoid arthritis, chronic pain, radiculopathy, asthma, ulcerous colitis, dermatitis (Ameri A., 1999 ref. as quoted).

Furthermore, nowadays there are numerous other symptoms or pathologies for which recent experimental evidence suggests a potential medical-therapeutic use of THC derivatives. This is the case of multiple sclerosis, a pathology in which cannabinoids are potentially capable of exerting not only anti-inflammatory but also anti-spastic effects, thus suggesting a pharmacological effect on muscle tone control (Baker D. et. al. 2000, Nature 404, 84-87; Ameri A. 1999 ref. as quoted).

Other promising fields involving the neuroprotective and anticonvulsant properties of cannabinoids and the relative derivatives include the ictus or cerebral and spinal trauma therapy sectors. Furthermore and consistently at CNS levels, existing experimental evidence goes to show that cannabimimetic derivatives could be of interest in association with other drugs (e.g. opioids) for pain therapy (Mas-Nieto M. et al. 2001, Brit. J. Pharmacol. 132: 1809-16).

Due to their bronchodilator and anti-hypertensive properties, they are held as promising in the fields of respiratory and/or cardiovascular insufficiency and hypertension therapy (Ameri A. 1999 ref. as quoted) whilst, considering their efficiency in as far as both the inhibition of cancer cell growth and cancer cell death promotion (anti-proliferation and pro-apoptotic effect) is concerned, they are also held as being promising in cancer therapies (Amen A. 1999 ref. as quoted).

There is furthermore a considerable quantity of evidence, even if anecdotal, concerning beneficial implementation of THC or derivatives thereof both in stimulating appetite in patients affected by AIDS wasting syndrome (Amen A. 1999 ref. as quoted) and in reducing nausea and vomit in cancer patients receiving chemotherapy (anti-emetic effect) (Ameri A. 1999 ref. as quoted), thus suggesting the effects thereof on appetite control.

Finally, endocannabinoid-like molecules such as palmitoyl ethanolamide (PEA) have been described as having inhibitory effects on the IgE-mediated release of mastocyte mediators, thereby indicating a possible role of said molecules in the relief of allergic conditions (Facci L. et al. 1995 Proc. Natl. Acad. Sci. USA Vol 92: 3376-80).

Nevertheless, although THC derivatives and THC itself appear to be very promising from an experimental point of view, currently the only approved clinical use thereof is for the reduction of intraocular pressure in patients with glaucoma (Ameri A. 1999 ref. as quoted).

Parallel to the above-mentioned experimental evidence leading to the assumption of various different clinical applications for cannabinoid derivatives, over the last few years the studies on the possible mechanisms of action of these molecules have undergone sudden acceleration with the discovery of the existence of specific THC receptors (termed CB receptors) in 1990 and of endogenous ligands for said receptors (termed endocannabinoids) in 1992.

To date, although a new receptor termed GPR55 has recently been identified and characterised showing a nanomole affinity array as to THC and PEA (Ryberg E, et al. Br J Pharmacol. 2007 Sep. 17; e-pub. ahead of print), the receptors considered as being involved in the mediation of the effects of THC and the related synthetic derivatives are two: receptor CB1, prevalently expressed on the nervous system as well as on some peripheral tissue (Piomelli D. et al. 2000, TIPS 21: 218-24) and receptor CB2, predominantly present in immune system cells of mammals and identified for the first time only in 1993 (Piomelli D. et al. 2000 ref. as quoted). Furthermore, notwithstanding the identification of receptor GRP55, there is evidence of the existence of further CB receptors that have not yet been characterised (Wiley J. L., Martin B. R. 2002, Chem. Phys. Lipids 121: 57-63).

Following the discovery of receptor CB1, the first endogenous compound capable of selective binding with said receptor was isolated from pig brain in 1992. Said compound, constituted by the amide between arachidonic acid and ethanolamine, two ubiquitous components of animal cellular membranes, was termed anandamide, thereby suggesting a role of cannabimimetic type endogenous mediators for this class of molecules, i.e. the N-acylamides (Martin et al. 1999, Life Sci. 65, 573-595). Another type of molecule was subsequently isolated, pertaining to the class of intermediate metabolics known as monoacylglycerols, i.e. 2-arachidonoylglycerol having cannabimimetic activities and high CB1 and CB2 receptor affinity (Martin et al. 1999 ref. as quoted). Finally, the last endocannabinoid isolated and characterised appears very much like the previous one, 2-arachidonoylglycerol, but with the arachidonic radical ethereally bound to carbon 2 of the glycerol (Harms L. et al. 2001 Proc. Natl. Acad. Sci. USA Vol 98, 3662-5). Experimental studies with said molecules suggest that although the three endocannabinoids identified are characterised by different functional groups, all three of them are capable of interacting with the CB1 and CB2 receptors, albeit with different affinities, and with effects that can be superimposed to the effects of natural cannabinoids such as THC and the synthetic derivatives thereof (Martin et al. 1999 ref. as quoted). Finally, experimental evidence gathered over the last few years leads to the assumption that this family of molecules (endocannabinoids) also interacts with the vanilloid receptor (TRPV) (De Petrocellis et al. 2000, Chem. Phys Lipids; 108, 191-209), whereas it has only shortly been known that cannabimimetic molecules that can be traced back to the aminoalkylindole class (for example WIN 55.212) are capable of interacting, other than with the CB receptors, also with other known receptors (e.g. the 5-HT3a receptor) (Barann M. et al 2002, Brit. J. Pharmacol.:137, 589-96). It is not possible therefore to exclude that endocannabinoids can interact with many other receptor or enzymatic systems. Said discoveries have, over the last few years, animated a considerable amount of scientific research on cannabinoids and endocannabinoids, not only resulting in considerable progress on the potential therapeutic role of cannabinoids and their derivatives but also leading to the synthesis and development of various different compounds capable of acting as receptor agonists and/or of strengthening the effects of endocannabinoids by interfering, for example, with the enzymes involved in the synthesis and degradation of endocannabinoids as well as with the cell systems involved in the release and re-uptake thereof.

By way of example, here below are a set of exemplary compounds to which cannabinoid-like activities can be attributed: a) THC derivatives (e.g. HU210, CP55940) (Patel S. and Hillard C. J. 2001, J. Pharmacol. Exp. Ther. 297, 629-37); b) aminoalkylindole derivatives (e.g. WIN 55.212) (Patel S. and Hillard C. J. 2001, ref. as quoted); c) saturated and unsaturated endocannabinoid derivatives (e.g. oylethanolamide OEA, palmitoyl ethanolamide PEA, methanandamide, olvanil, arvanil, NADA) (Calignano A. et al. 2001, Eur. J. Pharmacol. 419, 191-198); d) inhibitors of the FAAH, fatty acid amido-hydrolase enzyme, (e.g. AM 374) (Gifford A. N. et al. 1999, Eur. J. Pharmacol. 383, 9-14); e) endocannabinoid re-uptake inhibitors (e.g. AM404) (Giuffrida A. et al. 2001, J. Pharmacol. Exp. Ther., 298, 7-14). To date some receptor antagonists have been furthermore synthesised and developed for known receptors such as CB1 and CB2, (e.g. SR141716 and SR144528) (Francisco M. E. et al. 2002, J. Med. Chem. 45, 2708-19).

Although molecules have been synthesised for the purpose of obtaining compounds having specific agonist activities for the peripheral CB2 receptor (i.e. the receptor held as being involved in the control of peripheral inflammatory processes), the results obtained to date can be held as being modest due to the fact that in many cases said derivatives interact, albeit with minor yet not negligible affinity, with central receptor CB1, or likewise PEA or anandamide derivatives having a number of double bonds less than 4, as well as inferior homologues (e.g. stearoyl ethanolamide SEA, OEA) show central type effects when administered in vivo (Lambert D. M. Di Marzo V 1999, Curr. Med. Chem. 6, 757-73).

In this scenario the saturated N-acetyl-ethanolamide (NAE) represent a family of lipid derivatives that, although they do not present an appreciable affinity for the known cannabinoid receptors, are characterised by cannabinoid-like activity that is definitely of pharmacological interest.

Among said molecules, the most reknown and researched is surely palmitoyl ethanolamide (PEA). It is in fact known as of the 1950's that said molecule features various different pharmacologic activities (see above) and particularly anti-inflammatory activities. (Ganley O. H: et al. 1958; Perlik F. et al. 1971). PEA, prepared under the name of Impulsin, was widely used in humans in the 1970's (Masek K., et al., 1974 Europ. J. Clin. Pharmacol. 7, 415-419; Hurych J et al., 1980 Czecoslovak Medicine, 8, 218-225) for the prevention and remedy of diseases in the initial respiratory tract. In the 1990's, subsequent to the discovery of anandamide, PEA became popular again in that it was proven to be efficient for the reduction of mastocyte degranulation in various different experimental models (Facci L. ref. as quoted; Mazzari S., 1996, Eur J Pharmacol. 300, 227-36). It must furthermore be highlighted here that recent publications (Ryberg E., ref. as quoted) state that PEA shows a nano-mole affinity array for the recently identified receptor GPR55.

Perhaps due to its extremely scarce solubility in aqueous environments and although having been used for many years in cosmetic preparations as a pearlising agent commonly named Comperlan HS, the higher homologue of PEA, Stearoyl ethanolamide (SEA), has been subject to very little research in as far as its biologic activity is concerned. The small quantity of data available on the biologic activity of SEA are disclosed, in as far as anti-inflammatory activities are concerned, in three patents (U.S. Pat. Nos. 5,990,170; 5,679,667 and 5,506,224) where SEA consistently appears as being always much less active than the lower homologue PEA. It is furthermore reported that SEA interferes with the endocannabinoid system (Maccarrone et al. 2002 Biochem J. 366: 137-44. Maccarrone M. et al. 2002 Mol Cell Neurosci. 21:126-40) as well as with the expression of enzyme SCD-1 (Terrazzino S. et al. 2004 FASEB J. 18:1580-2).

Due to longstanding interest in the development of molecules deriving from the endocannabinoid class aimed at obtaining active compounds without any unwanted cannabinoid-like effects, the Applicant has surprisingly discovered that the association of the two PEA and SEA derivatives exerts a synergic action yielding anti-inflammatory effects in an immunogenic in vitro model of inflammation that are superior to those yielded by the single derivatives.

The subject of this invention therefore relates to the use of a PEA and SEA compound for the preparation of compositions for preventive therapeutic or paramedic treatment of pathologic conditions that can benefit from the endocannabinoid-like activities of said compounds.

The Applicant has in fact surprisingly found that the treatment in vitro with a mixed solution of the compounds according to the present invention develops a cannabimimetic pharmacological activity that is superior to that developed by the single components. The mixed solution can in fact be usefully used in pharmaceutical preparations for the treatment of pathologic conditions that can benefit from the preventive medical, therapeutic and paramedic use of cannabinoids/endocannabinoids.

The objects and advantages of the medical, therapeutic or paramedic use of said compound of saturated acyl derivatives condensed with ethanolamine in pathologic conditions that can be controlled by cannabinoids and by endocannabinoids or similar molecules according to the present invention, will be best understood by way of the following, detailed description.

The applicant has in fact found that, subsequent to in vitro treatment, the mixed solution according to the present invention enables the observation of a marked and highly significant reduction in the release of inflammatory mediators by mastocyte cells stimulated by way of immunogenic stimulation, indicating that the mixed solution according to the present invention develops a powerful anti-inflammatory activity.

More specifically, a RBL-2H3 mastocyte cell line was used to express high-affinity receptors for the IgE immunoglobulins. The interaction of the antigens with the IgE molecules present on the cell surface stimulates secretion by said cells of the pro-inflammatory contents of their intracytoplasmic granules, amongst which significant quantities of: histamine, leukotrienes, prostaglandins and TNF-alfa. The RBL-2H3 therefore represent an excellent cell module for the study of the mechanisms of exocytosis and release of the inflammatory mediators and of the relative modulation, as the case may be. In particular, measurement of the activity by the β-hexosaminidase enzyme was performed, the release of which correlates positively with the secretion of very strong pro-inflammatory mediators such as histamine and TNF-alfa.

Said results, taken on the whole and never recorded previously, prove that saturated acyl derivatives have cannabinoid/endocannabinoid-like effects. Considering the synergic effect occurring due to their association, said effects are probably achieved by different receptor systems.

Assessed in vitro, they are described in detail as follows.

a. In Vitro Assay of the Cannabinmimetic Anti-Inflammatory Effects

As already specified, a RBL-2H3 mastocyte cell line was used to express high-affinity receptors for the IgE immunoglobulins, whilst the assessment of cell vitality was recorded by way of the MTT method. The RBL-2H3 cell culture was started with a density amounting to 20,000 cells/well (96 wells) and incubated with IgE-anti-DNP. After about one hour, the antigen (DNP) was introduced into the culture, then after another 30 minutes the culture medium was harvested. Measurement of the activity by the β-hexosaminidase enzyme was performed on the harvested cells, the release of which correlated positively with the secretion of very strong pro-inflammatory mediators such as histamine and TNF-alfa. A reduction of the enzymatic activities in the culture medium signifies minor cell degranulation and thus minor anti-inflammatory activity. The molecules according to the patent application herein were solubilised in DMSO and both added in variable concentrations to the cell cultures 1 hour prior to the introduction of the antigen.

b. Results

The results duly recorded in terms of reduction of β-hexosaminidase release are listed in table 1 on the following page.

TABLE 1 inhibition of β-hexosaminidase release in culture medium deriving from stimulated RBL-2H3 cells.

| COMPOUNDS | INHIBITION OF β-HEXOSAMINIDASE RELEASE (% on test)) |
|---|---|
| TEST | 0.00 |
| Palmitoyl ethanolamide (PEA) (10 µM) | 23.6 |
| Stearoyl ethanolamide (SEA) (10 µM) | 25.3 |
| Desametazone (10 µM) | 40.2 |
| PEA/SEA (5M//5 µM) | 58.5 |
| PEA/SEA (3 µM/7 µM) | 57.2 |
| PEA/SEA (2 µM/8 µM) | 52.3 |
| PEA/SEA (1 µM/9 µM) | 54.2 |
| PEA/SEA (7 µM/3 µM) | 53.2 |
| PEA/SEA (8 µM/2 µM) | 51.5 |
| PEA/SEA (9 µM/1 µM) | 51.0 |

In consideration therefore of the cannabimimetic effects, in vitro, displayed by these molecules, the compounds of PEA and SEA according to the present invention can thus be usefully employed for the preparation of pharmaceutical formulations for the therapeutic treatment, either alone or in association with other elective therapeutic agents for specific pathologic conditions, such as, by way of example, antiepileptic, neuroleptic, atypical neuroleptic, antidepressant, dopaminergic, dopamine-agonist, gaba-agonist, ponderal overweight, memory improvement and anti-inflammatory/pain killer drugs (e.g. opioids, salicylics, pyrazolics, indolacetics, fenamics, arylpropionics, arylacetics, oxycams, pyrancarboxylics, glucocorticoids, anti-COX-2, nimesulide and acetaminophen) and of pathologic conditions that can benefit from a cannabimimetic effect such as, e.g.:

for their anti-inflammatory effects in chronic inflammatory pathologies occurring in different body sections comprising the skin, whether of the autoimmune type or not;

for the capacity they have of inhibiting mastocyte degranulation in the relief of allergic conditions.

The methods of administration that can be implemented for the preventive or therapeutic treatment of pathologic conditions according to the present invention can be by oral, parenteral, intramuscular, subcutaneous, intravenous, topical, transdermic, rectal, sublingual, and nasal administration. The compound according to the therapeutic use can be administered in pharmaceutical formulations combined with excipients, dispersants and thinner agents either already known or new, compatible with pharmaceutical uses, aimed at achieving optimised delivery of the active principle to the activity site for effects that can be quick, sustained or delayed in time. For this purpose it is therefore also possible to use pharmaceutical formulations at fast, sustained or slow release. Relative dosages depend on the seriousness of the pathology and the method of administration that has been selected, as well as on the current conditions of the patient (age, body weight, general health). For descriptive purposes according to the present invention but not limited thereto, the dosages in question can be comprised between 1 mg/kg of body weight and 50 mg/kg of body weight per die administrations, repeated for a period going from 2 to 16 weeks. Suitable oral administration can be by way of dispersible powder compounds, tablets, pills, either hard or soft gelatine capsules and suspensions; suitable forms of parenteral administration can be intramuscular, subcutaneous, intravenous and peridural by way of compounds in form of buffered water solutions, oily suspensions or lyophilized compounds dispersible in appropriate solvent solutions prior to administration; suitable topical or transdermic administration can be rectal, nasal or sublingual, by way of compounds in appropriate excipients or dispersants in forms of patches, suppositories, ovules, pessaries, aerosol or sprays.

By way of example, the invention herein is particularly useful in the preparation of pharmaceutical formulations useful for relief and prevention in the treatment of gynaecological pathologies such as non infective vulvovaginitis, lichen sclerosus, iperplasia squamosa, lichen simplex chronicus, lichen planus, psoriasis, dermatitis eczematous chronicus, vulvitis, irritant vulvar pathology, vulvodynia, vulvar craurosis, inflammatory vaginal pathology, vaginitis, nodular vaginitis, papillary vaginitis, cystic vaginitis, atrophic vaginitis, vulvar vestibulitis, vestibular erythema, adnexitis, salpingovariolysis, endometritis, chronic vaginitis, metritis, parametritis. The composition can be in form of vaginal gel, according to the following formulation as per the given ratios:

| Butylene glycol | 10-50% |
|---|---|
| Water | 50-90% |
| Sodium propyl acrylate or hydroxyl propyl cellulose | 0.1-0.5% |

The composition herein is also particularly suitable for use in the preparation of pharmaceutical formulations useful in the relief and prevention of skin pathologies, such as dermatitis, atopic dermatitis, contact dermatitits, dermatitis herpetiformis, allergic dermatitis, seborrheic dermatitis, acantolytic dermatosis or Grover's disease, penfigo buloso, psoriasis, benign lichenoid keratosis, Henoch-Schonlein purpura, lupus erythematosus, necrobiosis lipoidica diabeticorum, penfigo vulgar, eosinophilic fasciitis, erythema nodosum, pruritis, hives, urticaria pigmentosa, urticaria papulosa, xantomatosis, systemic sclerosis, Sweet's syndrome, Sjögren's syndrome, sarcoidosis, eczema, discoid or nummular eczema, intertrigo, discoid lupus erythematosus, lichen simplex, lichen planus, varicose eczema, dyshidrotic eczema, dry skin, primary irritant dermatitis, nappy dermatitis, photodermatitis, nodular prurigo, skin lymphoma. Said pharmaceutical formulation is preferably in the form of a protective skin cream, comprising compounds present in the formulation at the given ratios:

| Propylene glycol | 40-50% |
|---|---|
| Water | 40-50% |
| Polysorbate 60 | 1-5% |

| | |
|---|---|
| Isopropyl myristate | 1-5% |
| Glyceryl monostearate | 1-10% |
| Sodium propyl acrylate | 0.1-0.5% |

The composition can furthermore be particularly useful also in the form of a gel emulsion, where the following compounds are present in the formulation at the given ratios:

| | |
|---|---|
| Propylene glycol | 40-50% |
| Water | 40-50% |
| Glyceryl monostearate | 1-10% |
| Sodium poly acrylate | 0.1-0.5%. |

What is claimed is:

1. A pharmaceutical formulation comprising:
a blend of palmitoyl ethanolamide (PEA) and stearoyl ethanolamide (SEA) compounds as active principles and a pharmaceutically acceptable excipient in effective amounts for treatment of a skin inflammatory pathology.

2. The pharmaceutical formulation according to claim 1, wherein said formulation or preparation is provided in a form suitable for topical or transdermic administration.

3. The pharmaceutical formulation according to claim 1, wherein said formulation or preparation is provided in a form suitable for topical or transdermic administration, and wherein said formulation or preparation is in the form of patches, aerosol, spray, emulsions, suspensions, or solutions.

4. The pharmaceutical formulation according to claim 1, wherein said formulation or preparation is in the form of suspensions, emulsions, or solutions.

5. The pharmaceutical formulation according to claim 1, wherein said formulation or other preparation is in the form of buffered water solutions, oily suspensions, solutions, or lyophilized powder dispersible in appropriate solvent solutions directly prior to administration.

6. A method of relief of inflammatory skin pathologies, the method comprising:
applying a formulation to an inflammatory skin pathology, said formulation comprising a blend of palmitoyl ethanolamide (PEA) and stearoyl ethanolamide (SEA) compounds as active principles and in effective amounts.

7. The method of claim 6, wherein said skin pathology comprises a chronic inflammatory skin pathology.

8. The pharmaceutical formulation according to claim 1, wherein said formulation or preparation is provided in the form of a gel emulsion.

9. The pharmaceutical formulation according to claim 5, wherein said formulation or preparation is provided in the form of a protective skin cream.

* * * * *